(12) United States Patent
Al-Sadah et al.

(10) Patent No.: US 9,006,677 B2
(45) Date of Patent: Apr. 14, 2015

(54) FAN BEAM MODULATOR FOR ION BEAMS PROVIDING CONTINUOUS INTENSITY MODULATION

(75) Inventors: Jihad H. Al-Sadah, Dhahran (SA); Thomas R. Mackie, Verona, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 1123 days.

(21) Appl. No.: 12/374,778

(22) PCT Filed: Feb. 27, 2008

(86) PCT No.: PCT/US2008/055104
§ 371 (c)(1),
(2), (4) Date: Jan. 22, 2009

(87) PCT Pub. No.: WO2008/106500
PCT Pub. Date: Sep. 4, 2008

(65) Prior Publication Data
US 2010/0019167 A1   Jan. 28, 2010

Related U.S. Application Data

(60) Provisional application No. 60/891,859, filed on Feb. 27, 2007.

(51) Int. Cl.
*G21K 5/04* (2006.01)
*A61N 5/10* (2006.01)
*G21K 1/04* (2006.01)
*G21K 1/10* (2006.01)

(52) U.S. Cl.
CPC ............... *A61N 5/1042* (2013.01); *A61N 5/103* (2013.01); *A61N 2005/1087* (2013.01); *A61N 2005/1095* (2013.01); *G21K 1/046* (2013.01); *G21K 1/10* (2013.01)

(58) Field of Classification Search
USPC ........... 250/491.1, 492.1, 492.3, 505.1, 515.1
See application file for complete search history.

(56) References Cited

U.S. PATENT DOCUMENTS

| 4,276,477 A | 6/1981 | Enge |
| 4,868,843 A * | 9/1989 | Nunan .......................... 378/152 |
| 5,317,616 A | 5/1994 | Swerdloff et al. |
| 5,394,452 A | 2/1995 | Swerdloff et al. |

(Continued)

FOREIGN PATENT DOCUMENTS

| EP | 0986070 A | 3/2000 |
| EP | 1045399 A | 10/2000 |

(Continued)

OTHER PUBLICATIONS

International Search Report, PCT Application No. PCT/US2008/055104, dated Jul. 17, 2008, ISA/EPO, 2280 HV Rijswijk, NL.

(Continued)

*Primary Examiner* — Nicole Ippolito
(74) *Attorney, Agent, or Firm* — Boyle Fredrickson, S.C.

(57) ABSTRACT

An intensity modulator for controlling the intensity of ions, such as protons, controllably block a portion of sub-areas of an area beam to control the average intensity within that sub-area. A fan beam is then created by a focusing process that reforms the area beam while blurring intensity variations in each sub-area to a corresponding beamlet in the fan beam of uniform intensity.

14 Claims, 2 Drawing Sheets

(56) References Cited

U.S. PATENT DOCUMENTS

| | | | |
|---|---|---|---|
| 5,442,675 | A | 8/1995 | Swerdloff et al. |
| 5,528,650 | A | 6/1996 | Swerdloff et al. |
| 5,548,627 | A | 8/1996 | Swerdloff et al. |
| 5,625,663 | A | 4/1997 | Swerdloff et al. |
| 5,661,773 | A | 8/1997 | Swerdloff et al. |
| 5,668,371 | A * | 9/1997 | Deasy et al. ............ 850/1 |
| 5,673,300 | A | 9/1997 | Reckwerdt et al. |
| 5,724,400 | A | 3/1998 | Swerdloff et al. |
| 5,802,136 | A | 9/1998 | Carol |
| 6,345,114 | B1 | 2/2002 | Mackie et al. |
| 6,385,286 | B1 | 5/2002 | Fitchard et al. |
| 6,438,202 | B1 | 8/2002 | Olivera et al. |
| 6,560,311 | B1 | 5/2003 | Shepherd et al. |
| 6,618,467 | B1 | 9/2003 | Ruchala |
| 6,636,622 | B2 | 10/2003 | Mackie et al. |
| 6,661,870 | B2 | 12/2003 | Kapotoes et al. |
| 6,731,970 | B2 | 5/2004 | Scholssbauer et al. |
| 6,891,177 | B1 * | 5/2005 | Kraft et al. ............ 250/505.1 |
| 6,915,005 | B1 | 7/2005 | Ruchala et al. |
| 7,046,831 | B2 | 5/2006 | Ruchala et al. |
| 7,186,986 | B2 | 3/2007 | Hinderer et al. |
| 7,207,715 | B2 | 4/2007 | Yue |
| 7,302,038 | B2 | 11/2007 | Mackie |
| 2002/0136439 | A1 | 9/2002 | Ruchala et al. |
| 2003/0160189 | A1 | 8/2003 | Matsuda |
| 2003/0198319 | A1 | 10/2003 | Toth et al. |
| 2005/0029471 | A1 * | 2/2005 | Kraft et al. ............ 250/492.1 |
| 2005/0123092 | A1 | 6/2005 | Mistretta et al. |
| 2005/0197564 | A1 | 9/2005 | Dempsey |
| 2006/0226372 | A1 | 10/2006 | Yanagisawa |
| 2006/0285639 | A1 | 12/2006 | Olivera et al. |
| 2007/0029510 | A1 | 2/2007 | Hermann |
| 2007/0036267 | A1 | 2/2007 | Becker et al. |
| 2007/0041494 | A1 | 2/2007 | Ruchala et al. |
| 2007/0041495 | A1 | 2/2007 | Olivera et al. |
| 2007/0041496 | A1 | 2/2007 | Olivera et al. |
| 2007/0041497 | A1 | 2/2007 | Schnarr et al. |
| 2007/0041498 | A1 | 2/2007 | Olivera et al. |
| 2007/0041499 | A1 | 2/2007 | Lu et al. |
| 2007/0041500 | A1 | 2/2007 | Olivera et al. |
| 2007/0043286 | A1 | 2/2007 | Lu et al. |
| 2007/0076846 | A1 | 4/2007 | Ruchala et al. |
| 2007/0104316 | A1 | 5/2007 | Ruchala et al. |
| 2007/0195922 | A1 | 8/2007 | Mackie et al. |
| 2007/0195929 | A1 | 8/2007 | Ruchala et al. |
| 2007/0195930 | A1 | 8/2007 | Kapatoes et al. |
| 2007/0242801 | A1 | 10/2007 | Mackie et al. |

FOREIGN PATENT DOCUMENTS

| | | |
|---|---|---|
| JP | 2000 214298 A | 8/2000 |
| WO | WO02/07817 A | 1/2002 |
| WO | WO02/41948 A | 5/2002 |
| WO | WO2005/004168 A | 1/2005 |
| WO | WO2007/021226 A | 2/2007 |

OTHER PUBLICATIONS

International Search Report, PCT Application No. PCT/US2008/055070, dated Jul. 17, 2008, ISA/EPO, 2280 HV Rijswijk, NL.
International Search Report, PCT Application No. PCT/US2008/055069, dated Jul. 17, 2008, ISA/EPO, 2280 HV Rijswijk, NL.
International Search Report, PCT Application No. PCT/US2008/055161, dated Jul. 17, 2008, ISA/EPO, 2280 HV Rijswijk, NL.
International Search Report, PCT Application No. PCT/US2008/055083, dated Jul. 17, 2008, ISA/EPO, 2280 HV Rijswijk, NL.
International Search Report, PCT Application No. PCT/US2008/055096 dated Jul. 17, 2008, ISA/EPO, 2280 HV Rijswijk, NL.
International Search Report, PCT Application No. PCT/US2008/055090 dated Jul. 17, 2008, ISA/EPO, 2280 HV Rijswijk, NL.
International Search Report, PCT Application No. PCT/US2008/055147, dated Jul. 25, 2008, ISA/EPO, 2280 HV Rijswijk, NL.
Baumert, BG, et al., Dose conformation of intensity-modulated stereotactic photon beams, proton beams, and intensity-modulated proton beams for intracranial lesions, Int. J. Radiat. Oncol. Biol. Phys., 2005, 60:1314-1324, Elsevier, Amsterdam, Netherlands.
Deasy, JO, et al., Distal edge tracking: a proposed delivery method for conformal proton therapy using intensity modulation, 1997, pp. 406-409, Proceedings of the XIIth International Congress on Computers in Radiotherapy May 27-30, 1997, Salt Lake City, IEEE Publishing, Los Alamitos, California, USA.
Deasy, JO, A proton dose calculation algorithm for conformal therapy simulations based on Moliere theory of lateral deflections, Med. Phys., Apr. 1998, 25:476-483, American Association of Physical Medicine, New York, New York.
Lomax, AJ, Intensity modulation methods for proton radiotherapy, Phys. Med. Biol., 1999 44:185-205, IOP Publishing Ltd., Bristol, UK.
Lomax, AJ, et al. Intensity modulated proton therapy: A clinical example, Mar. 2001, Med. Phys. 28:317-324, , American Association of Physical Medicine, New York, New York.
Lomax, AJ, Compensated and intensity-modulated proton therapy, in Palta J, and Mackie TR (eds), Intensity Modulated Radiation Therapy: The State of the Art, Nov. 2004, pp. 787-828, Medical Physics Publishing Madison, WI.
Lomax, AJ, et al., Treatment planning and verification of proton therapy using spot scanning: initial experiences. 2004a, Med. Phys. 31:3150-3157, American Association of Physical Medicine, New York, New York.
Lomax, AJ, et al., The clinical potential of intensity modulated proton therapy, 2004b, Z. Med. Phys. 14:147-152, Elsevier, Amsterdam, Netherlands.
Kanai, T, et al., Spot scanning system for proton radiotherapy, Jul./Aug. 1980, Med. Phys 7:365-369, American Association of Physical Medicine, New York, New York.
Moyers MF, (Proton therapy, Van Dyk (ed), The Modem Technology of Radiation Oncology, 1999, pp. 823-869, Medical Physics Publishing, Madison, WI.
Nill, S, et al., Inverse planning of intensity modulated proton therapy, 2004, Z Med. Phys. 14:35-40, Elsevier, Amsterdam, Netherlands.
Oelfke U, et al., Intensity modulated radiotherapy with charged particle beams: Studies of inverse treatment planning for rotation therapy. Jun. 2000, Med. Phys, 27:1246-1257, American Association of Physical Medicine, New York, New York.
Paganetti H, Proton Therapy: A Workshop Handout. 2005, Private Communication, Massachusetts General Hospital, Boston, MA.
Sampayan S, et al. Development of a compact radiography accelerator using dielectric wall accelerator technology, Jun. 6, 2005, Proceed. Int. Pulsed Power Conf. Monterey, CA, Lawrence Livermore Laboratory, Livermore, CA.
Wilson RW., Radiological use of fast protons. Nov. 1946, Radiology 47:487-491, Radiological Society of North America, Easton, Pennsylvania.
Yu C., Intensity modulated arc therapy with dynamic multileaf collimation: an alternative to tomotherapy, 1995, Phys. Med. Biol. 40:1435-1449, IOP Publishing Ltd., Bristol, UK.
Anferov V., Combined X-Y scanning magnet for conformal proton radiation therapy, Med. Phys. , Mar. 2005, 32:815-818, American Association of Physical Medicine, New York, New York.
Goitlein, M., Beam scanning for heavy charged particle radiotherapy, Nov./Dec. 1983, Med. Phys. 10 (6) pp. 831-840, American Association of Physical Medicine, New York, New York.

* cited by examiner

FAN BEAM MODULATOR FOR ION BEAMS PROVIDING CONTINUOUS INTENSITY MODULATION

CROSS-REFERENCE TO RELATED APPLICATIONS

This application claims the benefit of U.S. Provisional Application 60/891,859, filed Feb. 27, 2007 and PCT Application PCT/US2008/055104 filed Feb. 27, 2008, the disclosures of which are incorporated herein by reference.

STATEMENT REGARDING FEDERALLY SPONSORED RESEARCH OR DEVELOPMENT

This invention was made with United States government support awarded by the following agency: NIH CA088960. The United States government has certain rights in this invention.

BACKGROUND OF THE INVENTION

The present invention relates to radiation therapy systems using ions, such as protons, for the treatment of cancer and the like and, in particular, to a system providing improved modulation of a ion beam.

External beam radiation therapy may treat a tumor within the patient by directing high-energy radiation in one or more beams toward the tumor. Recent advanced external beam radiation systems, for example, as manufactured by Tomotherapy, Inc., treat a tumor with multiple x-ray fan beams directed at the patient over an angular range of 360°. Each of the beams is comprised of individually modulated beamlets whose intensities can be controlled so that the combined effect of the beamlets, over the range of angles, allows an arbitrarily complex treatment area to be defined.

X-rays deposit energy in tissue along the entire path between the x-ray source and the exit point in the patient. While judicious selection of the angles and intensities of the x-ray beamlets can minimize radiation applied to healthy tissue outside of the tumor, inevitability of irradiating healthy tissue along the path to the tumor has suggested the use of ions such as protons as a substitute for x-ray radiation. Unlike x-rays, protons may be controlled to stop within the tissue, reducing or eliminating exit dose through healthy tissue on the far side of the tumor. Further, the dose deposited by a proton beam is not uniform along the entrance path of the beam, but rises substantially to a "Bragg peak" near a point where the proton beam stops within the tissue. The placement of Bragg peaks inside the tumor allows for improved sparing of normal tissue for proton treatments relative to x-ray treatments.

Unlike x-rays, protons may be controlled to stop within the tissue, eliminating exit dose through healthy tissue on the far side of the tumor. Further, the dose deposited by a proton beam is not uniform along the entrance path of the beam, but rises substantially at a "Bragg peak" near a point where a proton stops within the tissue. Proton therapy is described generally in U.S. Pat. No. 5,668,371 entitled "Method and Apparatus for Proton Therapy" issued Sep. 16, 1997, assigned to the assignee of the present invention and hereby incorporated by reference.

In distinction from x-rays, with protons it is possible to separately control intensity (i.e., the average number of protons per time over an area) and energy (i.e., the speed of the protons). Control of the intensity of protons determines the dose delivered by the protons to the tissue whereas control of the energy of the protons determines the depth in the tissue at which the dose is concentrated. In the above reference patent application, the intensity of the protons within different "beamlets" of a fan beam are controlled by changing the time during which blocking shutters are placed in the path of each beamlet versus the time the blocking shutters are removed from the path of the beamlets. By "duty cycle" modulating, the shutter intensity variations may be obtained.

A similar approach may be adopted in proton therapy systems that use a steerable pencil beam (rather than a fan beam) of protons. In this case the "dwell time" of the pencil beam at a particular location before it is moved determines the intensity of protons delivered to that location.

Both of these approaches will be termed "time accumulation" approaches as they rely on changing the length of time the tissue is exposed (and thus the average intensity of the beam) to control the dose. A drawback to such time accumulation systems is that higher average intensities require correspondingly increased exposure times. As a practical matter this increases treatment times. Designing fast acting shutters or pencil beam scanning systems, that might offset these increased treatment times, can be difficult or expensive.

BRIEF SUMMARY OF THE INVENTION

The present inventors have developed a shutter system that controls the instantaneous intensity of the ion beam and thus that need not entirely, or at all, rely on time accumulation to vary average intensity. Instead, in the invention, a set of shutters each blocks different latitudinally separate beamlets of an area beam by varying longitudinal amounts. The area beam is then refocused to a fan beam and this refocusing process blurs the image of the shutter to provide for uniform proton intensity within the beamlet area. The result is a set of beamlets having uniform ion intensity within the beamlet and whose instantaneous ion intensities (as opposed to average intensities) may be continuously varied. Multiple adjacent shutters are used to provide similar control on adjacent beamlets.

Specifically, the present invention provides an intensity modulator for ions, the intensity modulator having an area beam generator producing an area beam of protons. The area beam is received by an intensity modulator occluding the area of beam with a set of latitudinally adjacent ion-blocking shutters controllably extended to different longitudinal distances according to a desired intensity of each beamlet of protons. The desired intensity is obtained by controlling the portion of the area beam occluded by a given shutter. The partially occluded area beam is then collapsed in the longitudinal direction by a lens system to form a fan beam directed toward the patient.

It is thus one object of the invention to provide for continuous control of instantaneous beamlet intensity within a fan beam.

The intensity modulator may be combined with an energy modulator having a set of latitudinally adjacent ion attenuating wedges controllably extended to different longitudinal distances according to a desired energy of a beamlet of protons defined by a portion of the area beam occludable by a given wedge.

It is thus another object of the invention to provide a system that can provide both independent instantaneous control of intensity and energy.

Each wedge may be matched to a corresponding second wedge providing mirror movement to the first wedge to, in combination, present a uniform thickness of material within the fan beam.

It is thus another object of the invention to provide for energy modulation that is uniform within the cross-section of the beamlet.

The lens system may be a pair of quadrupole lenses aligned in rotation with respect to the other about a common axis.

It is thus an object of the invention to provide for a simple lens system to produce a fan beam that minimizes the productions of neutrons.

The beam generator may be a scattering foil receiving a pencil beam to spread it into an area beam.

Thus it is an object of the invention to provide a simple method of converting a pencil proton beam obtained from a cyclotron or synchrotron into an area beam for modulation.

The invention may provide a gantry holding the modulator for rotation of the fan beam with respect to the patient about a longitudinal axis while controllably varying the longitudinal distances of the shutters.

It is thus another object of the invention to provide a treatment technique that works well with the continuous modulation that may be obtained by moving shutters, the treatment intensity sinograms used in such orbiting treatment being generally smoothly continuous to comport with achievable modulation with the shutters.

These particular features and advantages may apply to only some embodiments falling within the claims and thus do not define the scope of the invention.

DETAILED DESCRIPTION OF THE PREFERRED EMBODIMENT

Figure 1:
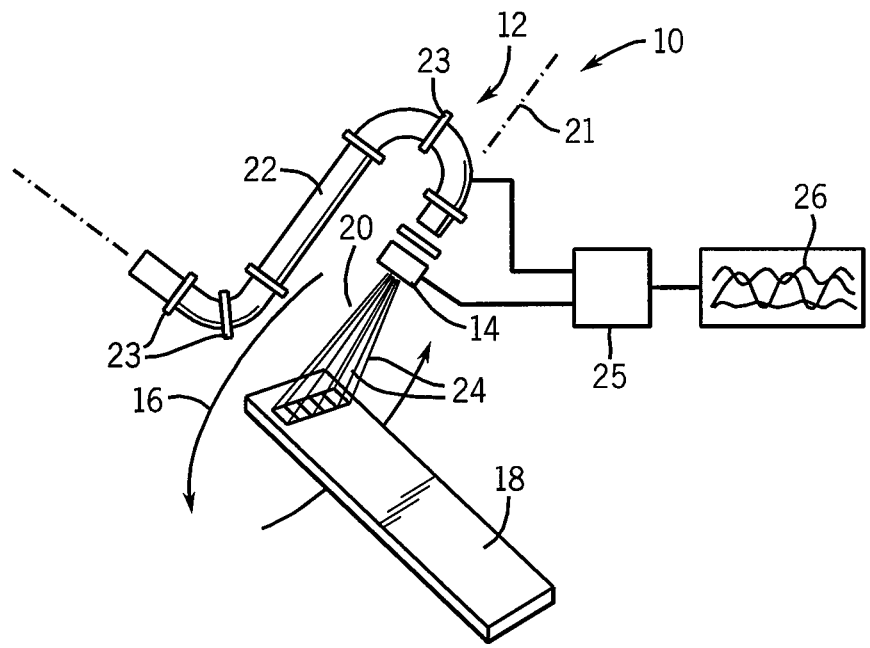
FIG. 1 is a simplified representation of a proton therapy machine suitable for use with the present invention and having a rotating gantry for directing a fan beam of protons toward a patient support at a range of angles, the beamlets of the fan beam controlled by a modulator.

Referring now to FIG. 1, a proton therapy machine 10 may include a gantry 12 having a modulator 14 that may orbit 16 about a patient (not shown) on a patient support table 18.

The modulator 14 receives a source of protons from a proton source conduit 22 that may receive a pencil beam of protons from a synchrotron, cyclotron or the like. The pencil beam of protons may be curved through the gantry 12 by means of bending magnets 23 to direct the pencil beam along axis 21 toward the patient support table 18 at all positions of the gantry 12 within the orbit 16.

During treatment, the pencil beam of protons is received by the modulator 14 which converts the pencil beam into a fan beam 20 and individually modulates beamlets 24 within the fan beam 20 in both energy and intensity. The energy and intensity of the beamlets 24 is under the control of a control computer 25 receiving control sinograms 26 providing data indicating desired intensities and energies of each individual beamlet 24 as a function of an angle of the gantry 12 within the orbit 16.

Figure 2:
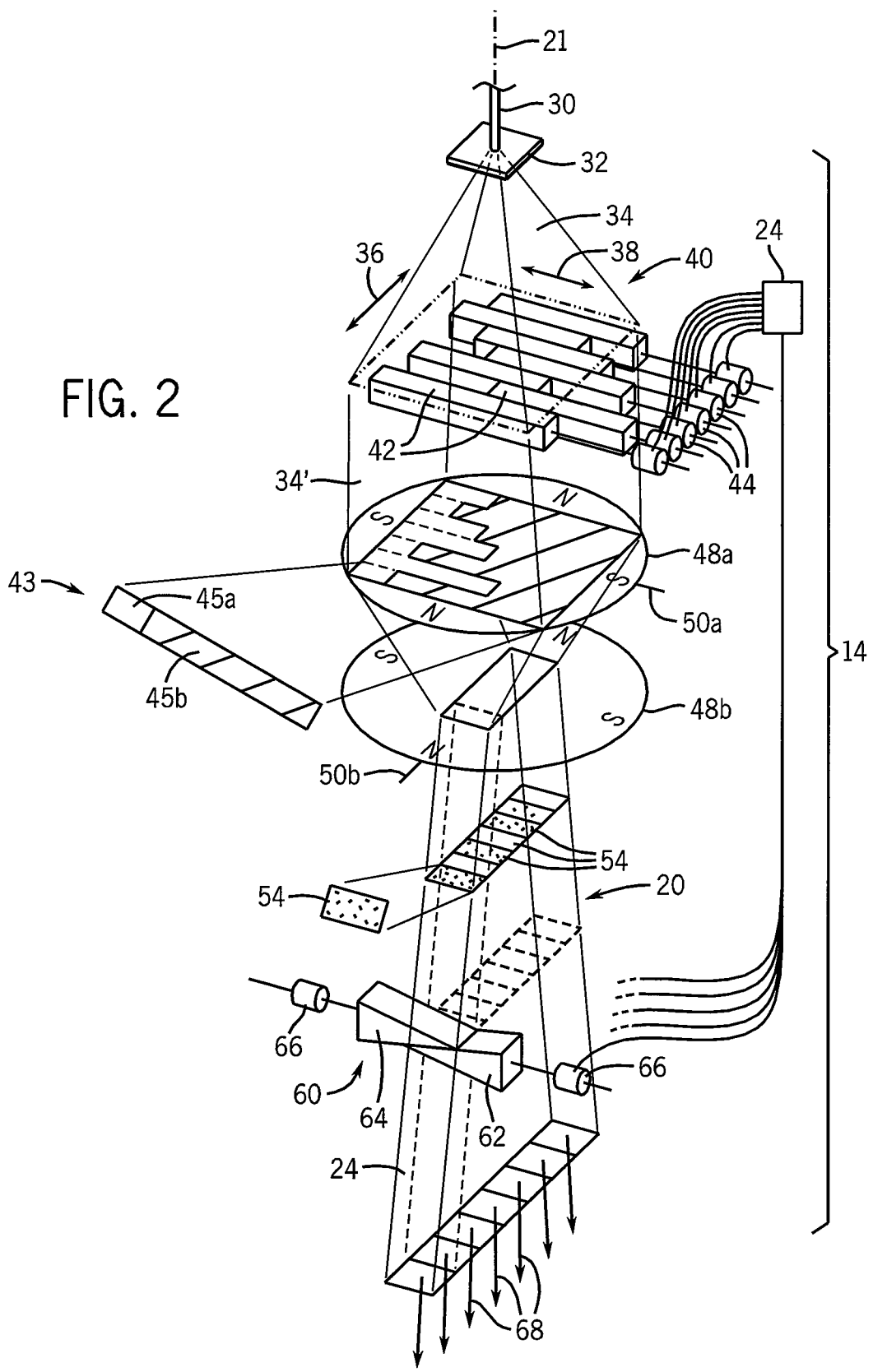
FIG. 2 is an exploded isometric representation of the modulator showing the various stages of intensity of the area beam and energy modulation of a fan beam.

Referring now to FIG. 2, the modulator 14 which rotates with the gantry 12, receives a pencil beam 30 along axis 21 at a scattering foil 32 or the like which spreads the pencil beam 30 into an area beam 34. The area beam 34 may be collimated to provide a generally rectangular cross-sectional area extending latitudinally 36 and longitudinally 38.

After collimation, the area beam 34 may be received by an intensity modulator 40 that provides for a set of latitudinally adjacent and longitudinally extending proton-opaque shutters 42. Each of the shutters 42 may, for example, be a rectangular block of ion blocking material (for example a dense metal) having its longest dimension aligned with the longitudinal direction and its latitudinal width defining the width of a beamlet 24. The shutters 42 may slide against each other at abutting latitudinal edges.

Each shutter 42 may be connected to an electronic or pneumatic actuator 44 controlled by the control computer 25 to move a distal end of the shutters 42 to different longitudinal distances within the area beam 34 while maintaining the proximal end of the shutters 42 outside of the area beam 34. As depicted, the actuators 44 are represented as motors (for example servomotors or stepper motors) connected to the shutters 42 by a machine screw mechanism. It will be understood that other well-known actuator systems including, for example, linear motors, pneumatic cylinders, or standard rotary motors with pulley or rack systems may be used in an open or closed loop fashion, the latter providing sensors such as optical or LVDT sensors, to close the feedback loop.

When all the shutters 42 are fully extended into the beam 34, they wholly block protons of the area beam 34. When all of the shutters 42 are wholly retracted, they allow unimpeded passage of the area beam 34. Normally the shutters 42 will partially block portions of the area beam 34 as determined by their extended length controlled by the actuator 44. In this latter case, the average intensity of the protons within an area 43 potentially occluded by a given shutter 42 will vary continuously depending on the percentage of this area blocked by the shutter 42 and thus the amount the shutter 42 has been extended into the area beam 34 by its actuator 44. The average intensity within this area 43 results from two regions of discontinuous intensity: one region 45a fully blocked by the shutter 42 and the other region 45b not blocked by the shutter 42. Thus, the intensity within this area 43 is not uniform.

The area beam 34' as modulated by the modulator 40 is then received by a lens array 46 comprised of two quadrupole magnet 48a and 48b of a type known in the art. Each quadrupole magnet 48a and 48b is aligned along the common axis 21 and aligned in rotation with respect to the other so that the first quadrupole magnet 48a has opposed north poles along an axis 50a and the second quadrupole magnet 48b, beneath the first quadrupole magnet 48a, has a corresponding axis 50b aligned with axis 50a.

The effect of this lens array 46 is that the area beam 34 is reformed into a fan beam 52. The fan beam 52 also extends along axis 21 but has a larger latitudinal dimension than the area beam 34' and a much narrower longitudinal dimension than the area beam 34'. As a result, each of the longitudinally extended areas 43 controlled by each shutter 42 in the intensity modulator 40 are compressed severely in the longitudinal direction. This compression creates the fan beam 20 of multiple controllable beamlets 24 each having an area 54 corresponding generally to one of the areas of 43.

The focusing effect of the lens array 46 also results in the discontinuous intensities of regions of 45a and 45b of areas 43 produced by the intensity modulator 40 being blurred so that the intensities of the beamlets 24 within the areas 54 are substantially uniform. The instantaneous intensity of the beamlets 24 in areas 54 thus will be equal to the average intensity of the beam in area 43 multiplied by the area of area 43 and divided by the area of area 54. This results from a substantially equal flux of protons passing through areas 43 and 54.

The lens system may be implemented by other elements including gratings and/or scattering foils and collimation plates to provide a blurring and collimation of the area beam into a fan beam (?).

Figure 3:
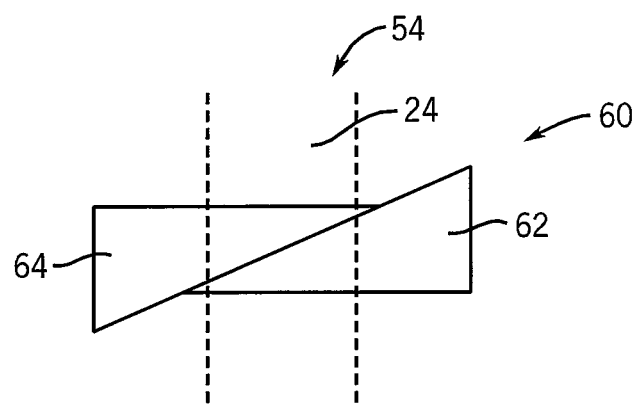
FIG. 3 is a side elevational view of one modulation element of an energy modulator of the present invention.

Each of the beamlets 24 defined by an area 54 is then received by an energy modulator 60. For clarity, only one energy modulation element of the energy modulator 60 for one beamlet 24 corresponding to a particular area 54 is depicted as also shown in FIG. 3. Each element of the energy modulator 60 provides for two opposed wedges 62 and 64 overlapping within the area 54 with their narrowest portions (measured along axis 21) directed toward each other.

Referring to FIG. 3, each wedge 62 and 64 may provide a right triangle of radiation attenuating material, with one wedge inverted with respect to the other along the longitudinal axis and rotated by 180° along the axis of the beamlet 24 so that their hypotenuses slide along each other and their bases remain parallel. In this way, a thickness of material of the combined wedges 62 and 64 within the fan beam 52 is constant throughout the area 54. The wedges 62 and 64 are each connected to actuators 66 which work to move the wedges 62 and 64 in opposite directions, both moving out of and into the beamlet 24 in synchrony so that the total thickness of the wedge material may be controlled. The wedges 62 and 64 serve only to slow the protons rather than block them completely and thus provide for energy modulation or range control of the protons indicated by arrows 68.

The actuators 66 also connect to the control computer 25 so that both the intensity and the energy of each beamlet within the fan beam 52 may be independently controlled during treatment.

It will be understood that these wedges need not be shaped like a wedge (necessary for uniform wedge material) but may be, for example, constructed of materials with variable attenuation to act like a wedge while being shaped differently.

It is specifically intended that the present invention not be limited to the embodiments and illustrations contained herein and the claims should be understood to include modified forms of those embodiments including portions of the embodiments and combinations of elements of different embodiments as come within the scope of the following claims.

We claim:

1. A method of modulating ions comprising:
   (a) generating an area beam of ions directed along an axis and having a longitudinal and latitudinal extent in cross-section and divided into latitudinally adjacent beamlets of ions;
   (b) occluding the area beam with a set of latitudinally arrayed ion-blocking shutters each having a latitudinal width substantially equal to a latitudinal width of a beamlet, the ion-blocking shutters controllably extended to different longitudinal distances at the cross-section according to a desired intensity of a beamlet of ions to block only a controllable portion of the longitudinal extent of the beamlet and to pass without blocking a remaining portion of the beamlet so that the intensity of the beamlet is substantially nonuniform in a longitudinal direction, some of the different longitudinal distances at the cross-section being less than a length of the longitudinal extent of the area beam; wherein an average intensity of the beamlet is defined by a portion of the beamlet occluded by a given shutter; and
   (c) refocussing the occluded area beam with a lens system to collapsing the area beam and beamlets in the longitudinal direction to form a fan beam directable toward a patient for radiation therapy to provide a substantially uniform longitudinal intensity in each collapsed beamlet.

2. The method of claim 1 further including the step of occluding the fan beam with a set of latitudinally adjacent ion attenuating wedges controllably extended to different longitudinal distances according to a desired energy of a beamlet of ions defined by a portion of the area beam occludable by a given wedge.

3. The method of claim 1 wherein each wedge is matched to a corresponding wedge providing mirror movement to the wedge to present a uniform thickness of material within the fan beam.

4. The method of claim 1 wherein step of the collapsing the area beam passes the area beam through a pair of quadrupole lenses aligned in rotation with each other about the axis.

5. The method of claim 1 wherein the step of generating the area beam passes a pencil beam through a scattering foil to form the area beam.

6. The method of claim 1 wherein the area beam is a proton beam.

7. The method of claim 1 including the step of rotating the fan beam with respect to the patient about a longitudinal axis while controllably varying the longitudinal distances of the shutters.

8. A modulator for ions comprising:
   (a) a beam generator generating an area beam of ions directed along an axis and having a longitudinal and latitudinal extent in cross-section composed of latitudinally adjacent beamlets of ions;
   (b) an intensity modulator occluding the area beam with a set of latitudinally arrayed ion-blocking shutters each having a latitudinal width substantially equal to a latitudinal width of a beamlet, the ion-blocking shutters controllably extended to different longitudinal distances at the cross-section according to a desired intensity of a beamlet of ions to block only a controllable portion of the longitudinal extent of the beamlet and to pass without blocking a remaining portion of the beamlet so that the intensity of the beamlet is substantially nonuniform in a longitudinal direction, some of the different longitudinal distances at the cross-section being less than a length of the longitudinal extent of the area beam; wherein an average intensity of the beamlet is defined by a portion of the beamlet occluded by a given shutter; and
   (c) a lens system receiving the area beam from the intensity modulator, the lens system collapsing the area beam and beamlets in the longitudinal direction to form a fan beam directable toward a patient for radiation therapy to provide a substantially uniform longitudinal intensity in each collapsed beamlet.

9. The modulator of claim 8 further including an energy modulator having a set of latitudinally adjacent ion attenuating wedges controllably extended to different longitudinal distances according to a desired energy of a beamlet of ions defined by a portion of the area beam occludable by a given wedge.

10. The modulator of claim 8 wherein each wedge is matched to a corresponding wedge providing minor movement to the wedge to present a uniform thickness of material within the fan beam.

11. The modulator of claim 8 wherein the lens system is a pair of quadrupole lenses aligned in rotation about the axis.

12. The modulator of claim 8 wherein the beam generator is a scattering foil receiving a pencil beam to spread it into an area beam.

13. The modulator of claim 8 wherein the beam generator generates a proton beam.

14. The modulator of claim 8 including a gantry holding the modulator for rotation of the fan beam with respect to the patient about a longitudinal axis while controllably varying the longitudinal distances of the shutters.

* * * * *